US005631224A

United States Patent [19]
Efendic et al.

[11] Patent Number: 5,631,224
[45] Date of Patent: May 20, 1997

[54] USE OF A PEPTIDE

[75] Inventors: Suad Efendic, Lindingö ; Mark Gutniak, Hässelby, both of Sweden; Ole Kirk, Virum, Denmark

[73] Assignee: Novo Nordisk A/S, Bagsvaerd, Denmark

[21] Appl. No.: 295,913

[22] PCT Filed: Mar. 18, 1993

[86] PCT No.: PCT/DK93/00099

§ 371 Date: Oct. 13, 1994

§ 102(e) Date: Oct. 13, 1994

[87] PCT Pub. No.: WO93/18786

PCT Pub. Date: Sep. 30, 1993

[30] Foreign Application Priority Data

Mar. 19, 1992 [DK] Denmark ................................. 0363/92

[51] Int. Cl.$^6$ ......................... A61K 38/26; C07K 14/605
[52] U.S. Cl. ................................. 514/12; 514/2; 530/308
[58] Field of Search ........................... 514/12, 2; 530/308

[56] References Cited

FOREIGN PATENT DOCUMENTS

| WO87/06941 | 11/1987 | WIPO . |
| WO90/11296 | 10/1990 | WIPO . |
| WO91/11457 | 8/1991 | WIPO . |

OTHER PUBLICATIONS

Parker et al., Diabetes, vol. 40, Suppl. 1, p. 237A (1991).

"The pharmacological basis of therapeutics", 8th ed. (A. Gilman et al., eds.) Pergamon Press, New York, 1990, pp. 1480–1487.

*Primary Examiner*—Paula K. Hutzell
*Assistant Examiner*—Benet Prickril
*Attorney, Agent, or Firm*—Steve T. Zelson, Esq.; Valeta A. Gregg, Esq.

[57] ABSTRACT

The invention employs GLP-1(7-37), GLP-1(7-36)amide, and certain related compounds in combination with an oral hypoglycaemic agent for treating diabetes mellitus.

12 Claims, No Drawings

USE OF A PEPTIDE

CROSS-REFERENCE TO RELATED APPLICATIONS

This application is a 371 of PCT/DK93/00099, filed Mar. 18, 1993, which is incorporated herein by reference.

FIELD OF THE INVENTION

The present invention relates to the use of GLP-1(7-37), GLP-1(7-36)amide, or certain related compounds for the preparation of a medicament for use in the treatment of diabetes in a regimen which additionally comprises treatment with an oral hypoglycaemic agent. The invention also relates to a method of treating diabetes by using said medicament.

BACKGROUND OF THE INVENTION

Diabetes is characterized by an impaired glucose metabolism manifesting itself among other things by an elevated blood glucose level in the diabetic patients. Underlying defects lead to a classification of diabetes into two major groups: type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with agents that stimulate β-cell function or with agents that enhance the tissue sensitivity of the patients towards insulin.

Among the agents applied for stimulation of the β-cell function, those acting on the ATP-dependent potassium channel of β-cells are most widely used in current therapy. The so-called sulfonylureas such as tolbutamide, glibenclamide, glipizide, and gliclazide are used extensively and other agents such as AG-EE 623 ZW also acting at this molecular site are under development (AG-EE 623 ZW is a company code for (S)-(+)-2-ethoxy-4-[2-[[3-methyl-1-[2-(1piperidinyl)phenyl]butyl]-amino]-2-oxoethyl]benzoic acid, a compound described in European patent publication No. 147,850 (to Dr. Karl Thomae GmbH)). Among the agents applied to enhance tissue sensitivity towards insulin metformin is a representative example.

Even though sulfonylureas are widely used in the treatment of NIDDM this therapy is, in most instances, not satisfactory: In a large number of NIDDM patients sulfonylureas do not suffice to normalize blood sugar levels and the patients are, therefore, at high risk for acquiring diabetic complications. Also, many patients gradually lose the ability to respond to treatment with sulfonylureas and are thus gradually forced into insulin treatment. This shift of patients from oral hypoglycaemic agents to insulin therapy is usually ascribed to exhaustion of the β-cells in NIDDM patients.

Over the years, numerous attempts have therefore been made to provide novel agents which stimulate β-cell function in order to offer the NIDDM patients an improved treatment. Recently, a series of peptides derived from glucagon-like peptide-1 have been considered as insulinotropic agents for therapeutic use.

Glucagon-like peptide-1, also referred to as GLP-1, is a peptide sequence found in the C-terminal portion of mammalian proglucagon. Prior to 1985, no definite biological activity of GLP-1 had been reported. However, in 1985 it was demonstrated that the amide of a fragment of GLP-1, namely GLP-1(1-36)amide, stimulates insulin release from isolated precultured rat pancreatic islets in the presence of glucose in a dose-dependent manner (Schmidt, W. E. et al. *Diabetologia* 28 (1985) 704–7). This finding suggests that GLP-1(1-36)amide and related peptides might be useful in the treatment of type 2 diabetes. Due to its substantially closer sequence homology to glucagon and glucosedependent insulinotropic peptide, also referred to as GIP, Schmidt et al. suggested that an even stronger glucagon- and/or GIP-like biological activity could be expected with GLP-1 (7-36) than with the intact peptide. In recent years, particular interest has focused on the GLP-1 fragments GLP-1(7-37) and GLP-1(7-36)amide and analogues and functional derivatives thereof. The designation GLP-1(1-36) indicates that the peptide fragment in question comprises the amino acid residues from (and including) number 1 to (and including) number 36 when counted from the N-terminal end of the parent peptide, GLP-1. Similarly, the designation GLP-1(7-37) designates that the fragment in question comprises the amino acid residues from (and including) number 7 to (and including) number 37 when counted from the N-terminal end of the parent peptide, GLP-1. The amino acid sequence of GLP-1(7-36)amide and of GLP-1(7-37) is given in formula I:

His—Ala—Glu—Gly—Thr—Phe—Thr—Ser—Asp—Val—Ser— (I)
Ser—Tyr—Leu—Glu—Gly—Gln—Ala—Ala—Lys—Glu—Phe—
Ile—Ala—Trp—Leu—Val—Lys—Gly—Arg—X (SEQ ID NO:1)

which shows GLP-1(7-36)amide when X is $NH_2$ and GLP-1(7-37) when X is Gly—OH.

That GLP-1(7-36)amide is indeed an insulinotropic agent in man has been demonstrated by Kreymann, B. et al. who infused this peptide into healthy volunteers and observed a significant rise in plasma insulin (*Lancet* 2 (1987) 1300–304).

The insulinotropic action of GLP-1(7-37) in diabetic as well as in nondiabetic subjects has been demonstrated by Nathan, D. M. et al. *Diabetes Care* 15 (1992) 270–76.

International Patent Application No. WO 87/06941 (to The General Hospital Corporation) relates to a peptide fragment which comprises GLP-1(7-37) and functional derivatives thereof and to its use as an insulinotropic agent.

International Patent Application No. 90/11296 (to The General Hospital Corporation) relates to a peptide fragment which comprises GLP-1(7-36) and functional derivatives thereof and has an insulinotropic activity which exceeds the insulinotropic activity of GLP-1(1-36) or GLP-1 (1-37) and to its use as an insulinotropic agent.

International Patent Application No. 91/11457 (to Buckley et al.) relates to effective analogs of the active GLP-1 peptides 7-34, 7-35, 7-36, and 7-37.

The effect of GLP-1(7-37) in combination with glibenclamide on insulin secretion from rat pancreatic islets was studied in vitro by Parker, J. C. et al. (*Diabetes* 40 (suppl. 1) (1991) 237 A). Only an additive effect of the two agents was observed.

However, to the best of the knowledge of the present inventors the surprising synergistic effect in vivo achieved by the combined use of an oral hypoglycaemic agent and a fragment of GLP-1 or an analogue or a functional derivative thereof has not previously been disclosed.

SUMMARY OF THE INVENTION

The present invention relates to the surprising finding that when GLP-1 related peptides are administered in combination with oral hypoglycaemic agents in general and with sulfonylureas in particular for treatment of type 2 diabetes, a synergistic effect is observed. This surprising observation has been made even in type 2 diabetic patients who fail to respond when sulfonylureas are administered alone.

Thus, in its broadest aspect the present invention relates to the use of GLP-1(7-37), GLP-1(7-36)amide, or a pharmaceutically acceptable peptide containing a fragment of the GLP-1(7-37) sequence, or an analogue or a functional derivative of such a peptide for the preparation of a medicament for use in the treatment of type 2 diabetes in a regimen which additionally comprises treatment with an oral hypoglycaemic agent and to a method of treating type 2 diabetes which method comprises administering an effective amount of GLP-1(7-37), GLP-1(7-36)amide, or a pharmaceutically acceptable peptide containing a fragment of the GLP-1(7-37) sequence, or an analogue or a functional derivative of such a peptide to a patient in a regimen which additionally comprises treatment with an oral hypoglycaemic agent.

In a first preferred embodiment, the present invention relates to the use of GLP-1(7-36)amide for the preparation of a medicament for use in the treatment of type 2 diabetes in a regimen which additionally comprises treatment with an oral hypoglycaemic agent.

In a further preferred embodiment, the present invention relates to the use of GLP-1(7-37) for the preparation of a medicament for use in the treatment of type 2 diabetes in a regimen which additionally comprises treatment with an oral hypoglycaemic agent.

In a further preferred embodiment, the present invention relates to the use of an analogue of GLP-1(7-37) for the preparation of a medicament for use in the treatment of type 2 diabetes in a regimen which additionally comprises treatment with an oral hypoglycaemic agent.

In a further preferred embodiment, the present invention relates to the use of a functional derivative of GLP-1(7-37) for the preparation of a medicament for use in the treatment of type 2 diabetes in a regimen which additionally comprises treatment with an oral hypoglycaemic agent.

In a further preferred embodiment, the present invention relates to the use of GLP-1(7-37) or a fragment thereof or an analogue or a functional derivative of any of these including GLP-1(7-36)amide for the preparation of a medicament for use in the treatment of type 2 diabetes in a regimen which additionally comprises treatment with tolbutamide.

In a further preferred embodiment, the present invention relates to the use of GLP-1(7-37) or a fragment thereof or an analogue or a functional derivative of any of these including GLP-1(7-36)amide for the preparation of a medicament for use in the treatment of type 2 diabetes in a regimen which additionally comprises treatment with glibenclamide.

In a further preferred embodiment, the present invention relates to the use of GLP-1(7-37) or a fragment thereof or an analogue or a functional derivative of any of these including GLP-1(7-36)amide for the preparation of a medicament for use in the treatment of type 2 diabetes in a regimen which additionally comprises treatment with glipizide.

In a further preferred embodiment, the present invention relates to the use of GLP-1(7-37) or a fragment thereof or an analogue or a functional derivative of any of these including GLP-1(7-36)amide for the preparation of a medicament for use in the treatment of type 2 diabetes in a regimen which additionally comprises treatment with gliclazide.

In a further preferred embodiment, the present invention relates to the use of GLP-1(7-37) or a fragment thereof or an analogue or a functional derivative of any of these including GLP-1(7-36)amide for the preparation of a medicament for use in the treatment of type 2 diabetes in a regimen which additionally comprises treatment with a biguanide.

In a further preferred embodiment, the present invention relates to the use of GLP-1(7-37) or a fragment thereof or an analogue or a functional derivative of any of these including GLP-1(7-36)amide for the preparation of a medicament for use in the treatment of type 2 diabetes in a regimen which additionally comprises treatment with metformin.

In a further preferred embodiment, the present invention relates to the use of GLP-1(7-37) or a fragment thereof or an analogue or a functional derivative of any of these including GLP-1(7-36)amide for the preparation of a medicament for use in the treatment of type 2 diabetes in a regimen which additionally comprises treatment with (S)-(+)-2-ethoxy-4-[2-[[3-methyl-1-[2-(1-piperidinyl)phenyl]butyl]amino]-2-oxoethyl]benzoic acid.

In this specification, analogues of GLP-1(7-37) or of GLP-1(7-36)amide, respectively, means peptides which differ from GLP-1(7-37) or from GLP-1(7-36)amide, respectively, in that at least one of the amino acid residues of GLP-1(7-37) or of GLP-1(7-36)amide, respectively, independently has been exchanged by another amino acid residue, preferably one which can be coded for by the genetic code. The definition also comprises the case when amino acid residues are added at or deleted from the N-terminal and/or the C-terminal end of the peptide. Preferably, the total number of such additions, deletions and exchanges does not exceed five, more preferred it does not exceed three.

DETAILED DESCRIPTION OF THE INVENTION

As mentioned above, patients treated with sulfonylureas gradually fail to respond to sulfonylurea treatment. It is generally accepted among those skilled in the art that this failure is due to exhaustion of β-cells which, accordingly, are unable to excrete insulin in response to glucose stimulation. Also, it is generally accepted that the efficacy of sulfonylureas is limited by the capacity of β-cells to produce and excrete insulin. Accordingly, one would not expect any additional therapeutic advantage by treating NIDDM patients with sulfonylureas and other agents stimulating β-cell function as well.

Our finding that NIDDM patients may advantageously be treated with GLP-1 related peptides in combination with sulfonylureas or other oral hypoglycaemic agents is therefore, indeed, surprising. In fact, we have found that concomitant treatment with oral hypoglycaemic agents and GLP-1 related peptides results in a synergistic response by the NIDDM patients: treatment with oral hypoglycaemic agents and GLP-1 related peptides gives rise to a metabolic response greater than the sum of the responses of either agents when applied alone. Even in cases of sulfonylurea failures, the oral agents have been found to significantly enhance efficacy of GLP-1 related peptides.

Combined treatment with GLP-1 related peptides and oral hypoglycaemic agents is thus novel, therapeutically useful, and surprising. Unforeseen, therapeutic advantages can be gained by treating the NIDDM patients with both types of drugs.

Among the GLP-1 related peptides that can thus be used in the treatment of type 2 diabetes GLP-1(7-37) and GLP-1(7-36)amide are particularly advantageous, as they are identical to the naturally occurring hormones. Shorter peptides comprising part of the GLP-1(7-37) sequence or analogues of such shorter peptides or analogues of GLP-1(7-37) itself or functional derivatives of any of these can also be used to advantage, since pharmacodynamic and pharmacokinetic properties can be changed according to patients' demand by modifying the GLP-1 related fragment.

The GLP-1 related peptides can be administered by methods currently available according to the invention for administration of peptides. Nasal application is particularly advantageous from a patient complience point of view. Details in this respect can be found in our copending Danish patent application No. DK 0364/92 relating to nasal administration of medicaments comprising GLP-1 related peptides which was filed simultaneously with the present application. The contents of said application is hereby incorporated in its entirety by reference. Administration by injection or infusion will be preferred in instances where a specific protracted plasma profile of the active peptide is required, and oral administration is preferred in instances where extent and kinetics of absorption is not a critical issue.

The oral hypoglycaemic agent used according to the invention can be any oral agent exhibiting a glucose lowering effect. Among these agents, those acting on the ATP-dependent potassium channel of the β-cells are preferred such as glibenclamide, glipizide, gliclazide and AG-EE 623 ZW. The peptides according to the invention may also advantageously be applied in combination with other oral agents such as metformin and related compounds or glucosidase inhibitors as, for example, acarbose.

The features disclosed in the present description, examples and claims may, both separately and in any combination thereof, be material for realizing this invention in diverse forms thereof. The invention is further illustrated by the following examples which are not to be construed as limiting, but merely as an illustration of some preferred features of the invention.

EXAMPLE 1

Synergistic Effect of GLP-1(7-36)amide and Glibenclamide in NIDDM Patients

Assays

Blood samples were collected in plastic tubes containing EDTA (0.048 ml, 0.34M) and Trasylol® (1000 IU Kallikrein inhibitor, obtained from Bayer, West Germany) and immediately placed on ice. The samples were centrifuged at 4° C. and the plasma was stored at −20° C. Blood glucose was measured by a glucose oxidase method according to A. S. Hugget and D. A. Nixon, Lancet 2 (1957) 368–370. Plasma C-peptide concentrations were determined by radioimmunoassay (RIA) using a commercially available kit. (Novo Research Institute, Denmark). Plasma glucagon concentrations were measured by RIA using antibody 30K as described by G. R. Faloona and R. H. Unger in B. M. Jaffe and Behrman, eds. *Methods of Hormone Radioimmunoassay*, Academic Press, New York (1974) 317–330.

For further experimental details (e.g. on calculation of isoglycaemic meal-related insulin response, IMIR), reference is made to M. Gutniak, C. Ørskov, J. J. Holst, B. Ahren and S. efendic, *The New England Journal of Medicine* 326 (29) (1992) 1316–1322, where a different experiment performed under similar conditions is described.

Methods

On four different days the effect of either injecting glibenclamide, 1 mg i.v., or infusing GLP-1 (7-36)amide at a rate of 0.75 pmol per kilogram of body weight per minute or a combination thereof was studied in the same group of 6 insulin treated obese NIDDM patients (Body Mass Index: 30.1±2.4 kg/m$^2$) and compared to administration of saline as control. Ordinary administration of insulin was stopped 24 hours before the administration of the test compounds or of the saline started and all subjects were fasted overnight. A Biostator (Miles, Diagnostic Division, Elkhart, Ind.) was used for insulin administration in this period in order to normalize blood glucose levels before the administration of the test compounds was initiated and also to keep a normal postprandial blood glucose pattern 180 minutes following the ingestion of a standard test meal comprising boiled potatoes, boiled beef, cooked carrots, a glass of milk containing 0.5% butterfat, and a slice of bread baked from a mixture of wheat and rye flours. In this meal, 28, 26, and 46% of the energy comes from protein, fat and carbohydrates, respectively. Administration of the test compounds was performed (glibenclamide, saline) or initiated (GLP-1 (7-36)amide, respectively, 30 minutes after normoglycaemia was achieved. The infusion of (GLP-1 (7-36)amide was continued for 210 minutes. After 30 minutes (time zero), the subjects were given the test meal which was consumed within 15 minutes. Blood samples were obtained at −30, 0, 15, 30, 90, 120, 150 and 180 minutes.

Results

After the ingestion of the meal, meal-related C-peptide response, glucagon response and isoglycaemic meal-related insulin requirement (IMIR) was measured. The results are summerized in Table 1.

TABLE 1

| | C-peptide response (pg/ml/210 min) | Glucagon response (pg/ml/210 min) | IMIR (U) |
|---|---|---|---|
| Control (saline) | 7.4 ± 3.6 | 269345 ± 6299 | 17.4 ± 2.8 |
| GLP-1(7-36)amide | 25 ± 9.8 | 10451 ± 5126 | 6.3 ± 2.0 |
| glibenclamide | 105 ± 53.9 | *) | 8.3 ± 1.0 |
| GLP-1(7-36)amide + glibenclamide | 184 ± 55.1 | 2526 ± 4873 | 2.7 ± 0.7 |

*) glibenclamide had no significant influence on glucagon release.

As indicated in the table, both GLP-1(7-36)amide and glibenclamide significantly increased meal-related C-peptide response (p<0.02) and when administered in combination exerted a clear synergistic effect. GLP-1(7-36) amide suppressed the glucagon response (p<0.01) while glibenclamide had no significant effect. However, in combination with GLP-1(7-36)amide the glucagon response was almost abolished. Finally, both glibenclamide and GLP-1(7-36)amide lowered IMIR and in combination IMIR was as low as 2.7±0.7.

In summary, this experiment demonstrates a strong synergistic effect of a combination of GLP-1(7-36)amide and glibenclamide.

EXAMPLE 2

Synergistic Effect of GLP-1(7-36)amide and Glibenclamide in NIDDM Patients with Secondary Failure to Sulfonylurea Treatment Methods Eight patients with NIDDM and secondary failure to sulfonylurea treatment participated in the study (age 57.6±2.7 years, body mass index 28.7±1.5 kg/m$^2$, diabetes duration 7.6±1.2 years, HbA$_{1c}$ 5.8±0.5). The diabetic patients fulfilled the criteria for NIDDM and IDDM according to the USA National Diabetes Data Group. None of the patients had impaired renal function, automatic neuropathy, or proliferative retinopathy, and all had normal liver function. They were instructed to eat a standard diet for diabetic patients at least 2 weeks before and during the study. The patients treated with sulfonylureas stopped their medication one week before the experiments. Those who were treated with insulin were instructed to stop the injections of NPH insulin 24 hours before the studies. Blood glucose concentrations were controlled with subcutaneous injections of regular insulin.

All the subjects were studied after an overnight fast. At 07.30 h on the morning of each study, three cannulas were inserted. One cannula was placed in an antecubital vein and was used to sample blood intermittently for hormone assays. It was flushed with saline after each sampling. A second cannula inserted retro-gradely in a dorsal hand vein was used for continuous monitoring of blood glucose concentrations. The venous blood was arterialized by heating the forearm and hand in a thermoregulated sleeve (Kanthal Medical Heating AB, Stockholm,, Sweden) at 45° C. The third cannula was inserted in the contralateral antecubital vein and was used for all infusions. From approximately 08.00 hours, the patients were connected to a Biostator in order to normalize their blood glucose concentrations. The algorithm of the Biostator was adjusted in order to normalize basal blood glucose levels. The target for blood glucose concentrations was 4–5 mmol/L. When the target was reached, the Biostator algorithm was changed to monitoring and the feedback insulin infusion was stopped. The experiments were started 30 minutes after normoglycemia was achieved, approximately 90 minutes after connection to the Biostator. An infusion of saline or 0.75 pmol/kg/min of GLP-1(7-36)amide (Peninsula Laboratories, St. Helens, Merseyside, England) then was started and continued for 210 minutes. In glibenclamide experiments an i.v. injection of 1 mg glibenclamide (Hoechst AG, Germany) was given at the same time point. These four studies were performed in a random order with 2–4 weeks elapsed between the experiments. At time 0 the subjects were given a standard lunch, as described in Example 1 which they ate within 15 minutes while sitting in bed. Blood samples were taken at FV, −60, −30, −15, 0, 15, 30, 90, 120, 150, and 180 minutes. Blood glucose was measured continuously.

Results

In the basal state, the effect on blood glucose and C-peptide levels was monitored 45 minutes after administration of GLP-1(7-36)amide, glibenclamide or a combination thereof had started. The results are summarized in Table 2.

TABLE 2

|  | Blood glucose mmol/l | C-peptide pmol/l |
|---|---|---|
| Control (saline) | 6.0 ± 0.3 | 0.53 ± 0.06 |
| GLP-1(7-36)amide | 5.1 ± 0.4 | 0.63 ± 0.1 |
| glibenclamide | 6.0 ± 0.3 | 0.56 ± 0.007 |
| GLP-1(7-36)amide + glibenclamide | 4.5 ± 0.1 | 0.72 ± 0.1 |

These results clearly demonstrates the synergistic effect of the two compounds as glibenclamide had no significant effect on its own while the effect of the combination of GLP-1(7-36)amide and glibenclamide, clearely, exeeded that of GLP-1(7-36)amide alone.

After the ingestion of the meal, the insulinogenic indices (integrated insulin/integrated glucose response) were calculated, again highlighting the synergistic effect of the two compounds, a shown in Table 3.

TABLE 3

|  | Insulinogenic index |
|---|---|
| Control (saline) | 1.6 ± 0.6 |
| GLP-1(7-36)amide | 21.0 ± 7.2, |
| glibenclamide | 10.6 ± 2.8, |
| GLP-1(7-36)amide + glibenclamide | 37.5 ± 9 |

We claim:

1. A method of treating diabetes which method comprises administering an effective amount of GLP-1(7-36)amide, GLP-1(7-37), or a fragment thereof which retains GLP-1(7-37)activity, to a patient in need of such a treatment in a regimen which additionally comprises treatment with an oral hypoglycaemic agent, wherein said hypoglycaemic agent is characterized as acting on an ATP-dependent potassium channel.

2. The method of claim 1 in which GLP-1(7-37) or GLP-1(7-36)amide is administered.

3. The method of claim 1 in which the oral hypoglycaemic agent is a blocker of the ATP-dependent potassium channel on β-cells.

4. The method of claim 1 in which the oral hypoglycaemic agent is a sulfonylurea.

5. The method of claim 1 in which the oral hypoglycaemic agent is (S)-(+)-2-ethoxy-4-[2-[[3-methyl-1-[2-(1-piperidinyl)phenyl]butyl]amino]-2-oxoethyl]benzoic acid.

6. The method of claim 1 in which the oral hypoglycaemic agent is a biguanide.

7. The method of claim 6 in which the oral hypoglycaemic is metformin.

8. The method of claim 2 in which the oral hypoglycaemic agent is a blocker of the ATP-dependent potassium channel on β-cells.

9. The method of claim 2 in which the oral hypoglycaemic agent is a sulfonylurea.

10. The method of claim 2 in which the oral hypoglycaemic agent is (S)-(+)-2-ethoxy-4-[2-[[3-methyl-1-[2-(1-piperidinyl)phenyl]butyl]amino]-2-oxoethyl]benzoic acid.

11. The method of claim 2 in which the oral hypoglycaemic agent is a biguanide.

12. The method of claim 11 in which the oral hypoglycaemic is metformin.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 31
        ( D ) OTHER INFORMATION: /note= "NH2 or Gly-OH"

( x i ) SEQUENCE DESCRIPTION: SEQ ID NO:1:

```
His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg Xaa
                 20                  25                  30
```